United States Patent [19]

Fujii

[11] Patent Number: 4,644,510

[45] Date of Patent: Feb. 17, 1987

[54] ULTRASONIC MEASUREMENT METHOD, AND APPARATUS THEREFOR

[75] Inventor: Tadashi Fujii, Fujinomiya, Japan

[73] Assignee: Terumo Kabushiki Kaisha, Tokyo, Japan

[21] Appl. No.: 711,954

[22] Filed: Mar. 14, 1985

[30] Foreign Application Priority Data

Mar. 17, 1984 [JP] Japan .................................. 59-50193

[51] Int. Cl.$^4$ ............................................. G01N 29/00
[52] U.S. Cl. ....................................... 367/87; 73/599; 73/602
[58] Field of Search ................... 367/87; 73/599, 602, 73/1 DV

[56] References Cited

U.S. PATENT DOCUMENTS 4,414,850 11/1983 Miwa et al. ........................... 73/599

OTHER PUBLICATIONS

"Quantitative Volume Backscatter Imaging", M. O'-Donnell IEEE Transactions on Sonics and Ultrasonics, vol. 30, #1 (1983).
"A Beam Corrected Estimation of the Frequency Dependent Attenuation of Biological Tissue from Backscattered Ultrasound", MJ. T. M. Cloostermans et al., Ultrasonic Imaging, vol. 5 (1983).
Handbook of Ultrasonic Technology, p. 49, The Nikkan Kogyo Shimbun Ltd.
"Oil-In-Gelatin Dispersions for use as Ultrasonically Tissue-Mimicking Materials" by Ernest L. Madsen, Ultrasound in Medicine AND Biology, vol. 8, No. 3 (1982).
"Tissue Mimicking materials for Ultrasound Phantoms" by Ernest L. Madsen in Medical Physics, vol. 5, No. 5 (1978).

Primary Examiner—Richard A. Farley
Attorney, Agent, or Firm—Frishauf, Holtz, Goodman & Woodward

[57] ABSTRACT

The acoustic characteristics, particularly the attenuation coefficient, internally of a object undergoing examination are measured on the basis of ultrasonic echo pulse, and diminishing the influence of the sound field. Standard media having attenuation coefficients that differ from one another are measured in advance by a predetermined method to find the attenuation rates and attenuation coefficients thereof. The attenuation coefficient of the object is taken to be the attenuation coefficient of one of the standard media that minimizes a difference between the attenuation rate of each standard media and the attenuation rate of the object, which is measured based on an ultrasonic echo signal from within the object.

8 Claims, 21 Drawing Figures

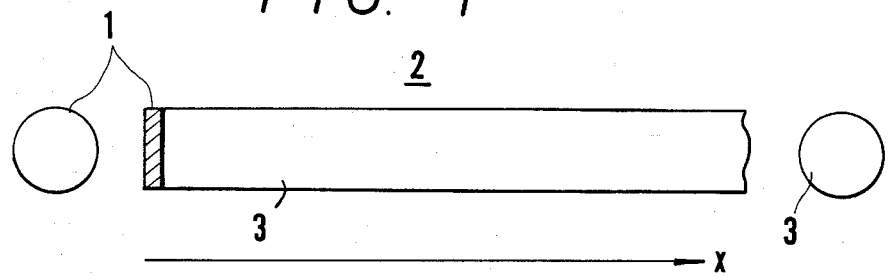
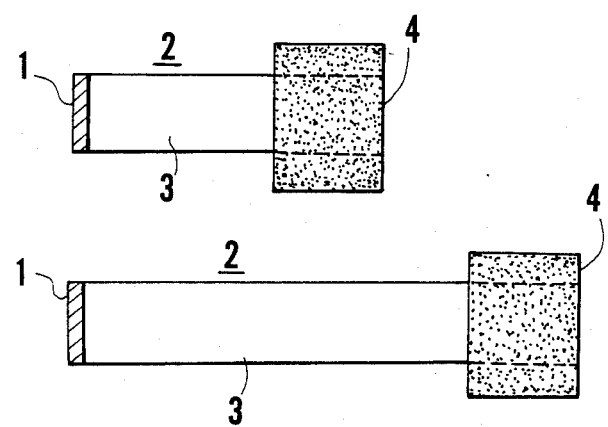

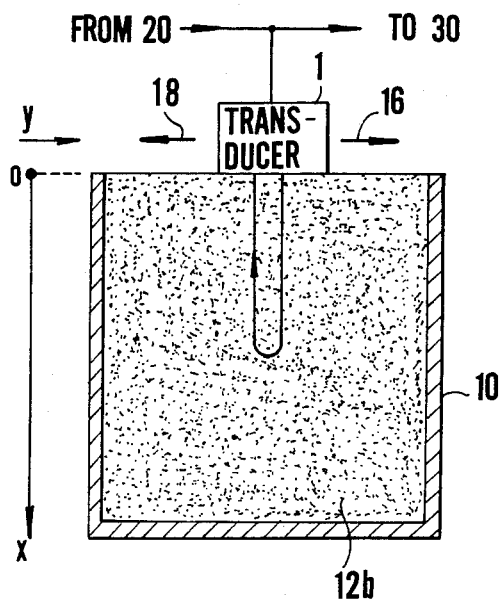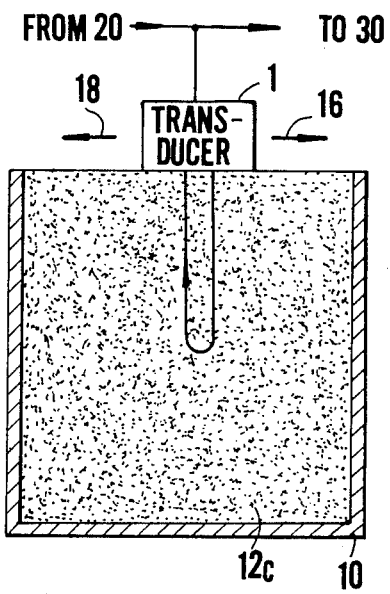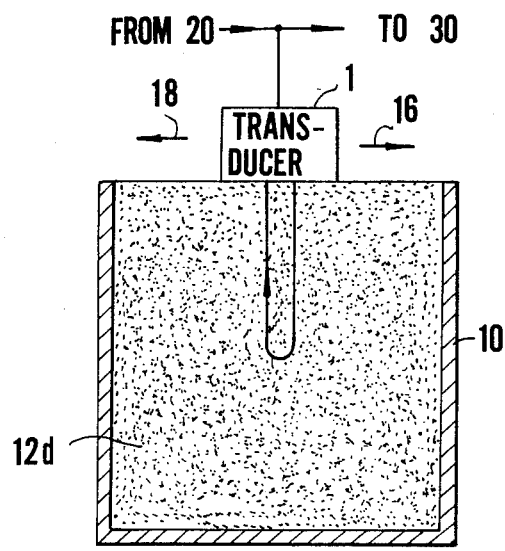

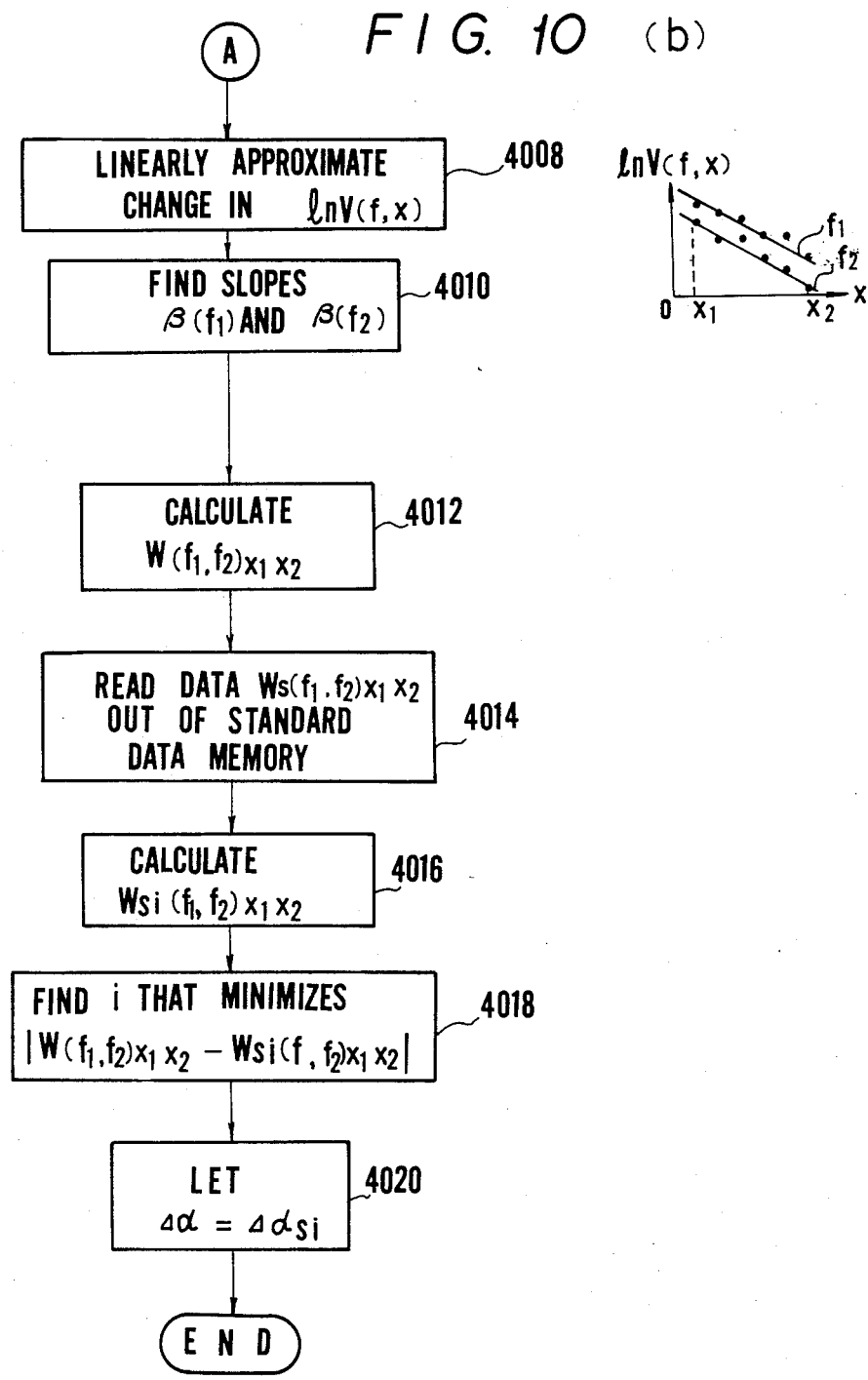

FIG. 11

| ΔαS1 | ΔαS2 | ΔαS3 |
|---|---|---|
| $W_{S1}(f_1, f_2)_1$ | $W_{S2}(f_1, f_2)_1$ | $W_{S3}(f_1, f_2)_1$ |
| $W_{S1}(f_1, f_2)_2$ | $W_{S2}(f_1, f_2)_2$ | $W_{S3}(f_1, f_2)_2$ |
| $W_{S1}(f_1, f_2)_3$ | $W_{S2}(f_1, f_2)_3$ | $W_{S3}(f_1, f_2)_3$ |
| $W_{S1}(f_1, f_2)_4$ | $W_{S2}(f_1, f_2)_4$ | $W_{S3}(f_1, f_2)_4$ |
| ⋮ | ⋮ | ⋮ |
| $W_{S1}(f_1, f_2)_{n-1}$ | $W_{S2}(f_1, f_2)_{n-1}$ | $W_{S3}(f_1, f_2)_{n-1}$ |
| $W_{S1}(f_1, f_2)_n$ | $W_{S2}(f_1, f_2)_{n-1}$ | $W_{S3}(f_1, f_2)_n$ |

Δx, X

ULTRASONIC MEASUREMENT METHOD, AND APPARATUS THEREFOR

BACKGROUND OF THE INVENTION

1. Field of the Invention

This invention relates to improvements in an ultrasonic measurement method and apparatus for subjecting an object to an ultrasonic transmission and receiving reflected ultrasonic waves from within the object to quantitatively measure the acoustic characteristics of the interior of the object. More particularly, the invention relates to an ultrasonic measurement method and apparatus for improving quantitatively the measurement of the acoustic characteristics of the object by correcting for an adverse effect upon the received ultrasonic waves caused by the transmission sound field characteristic of an ultrasonic transducer used to transmit and receive ultrasonic waves.

2. Description of the Prior Art

Ultrasonic measurement techniques find application widely in such fields as materials testing, sonar and medical diagnosis. In particular, ultrasound scanner systems for medical purposes have recently been developed. The principle of operation of an ultrasound scanner system resides in use of a pulse-echo method and utilizes a phenomenon wherein an ultrasonic pulse transmitted into a living body, which is the object undergoing measurement, is reflected at boundaries where there is a difference in acoustic impedance in the living body. The reflected wave (echo) is received and processed to display a tomograph of the living body by a so-called B-mode method. The echo therefore contains such information as the ultrasonic attenuation in the living body, acoustic impedance and propagation velocity of sound. Despite such a variety of effective information contained in the echo, however, the information being utilized at the present time is solely the amplitude of the echo.

More specifically, on the basis of assuming that the propagation velocity of sound in a living body is constant, attenuation ascribable to ultrasonic propagation in the living body is arbitrarily compensated by a so-called STC (sensitivity time control) circuit or TGC (time gain control) circuit, with the corrected echo signal being luminance-modulated and displayed as a tomograph on a cathode-ray tube. This is referred to as a "B-mode display". Accordingly, the tomograph obtained is nothing more than a qualitative picture of a two-dimensional distribution at a surface where the acoustic impedance in the living body is discontinuous, so that the morphological information relating to the position and shape of the bioligical tissue inevitably forms the core of the information utilized. However, the state of the art is such that information such as that relating to ultrasonic attenuation, which is a characteristic of the biological tissue, is not measured.

Several attempts at attaining attenuation information relating to biological tissue have been reported. However, a problem encountered in all of them is that the results of measurement depend upon the sound field characteristics of an ultrasonic beam transmitted by an ultransonic transducer used in measuring attenuation information, e.g. Specifically, as shown in FIG. 1, a transducer 1 of, e.g., a planar disc-shaped configuration transmits an ultrasonic beam 3 into a medium 2 which is a non-attenuating substance or a substance which exhibits very little attenuation. Here the medium 2 is assumed to be degassed water. If the ultrasonic beam 3 is a so-called pencil beam having a constant beam width and a constant sound pressure irrespective of propagation distance X from the transducer 1, then, even when an attenuating medium 4 is disposed at different distances from the transducer 1, as shown in FIG. 2, the characteristics (beam width, sound pressure) of the ultrasonic beam 3 incident upon the medium 4 will be the same despite the difference in distance. The influence of the sound field characteristics of the transmitted beam on the results of measurement can therefore be avoided. As well known, however, ultrasonic waves encounter an interference or diffraction phenomenon, with the result that the transmission sound field characteristic of, e.g., a disc transducer having a finite aperture defines a complicated pattern or field, as shown in FIGS. 3(a) through 3(c). FIG. 3(a) shows that almost all the ultrasonic energy lies within the limits shown therein. FIG. 3(b) shows that the distribution of the relative intensity $(Vx/Vm)^2$ along the central axis of the beam, where amplitude Vx is sound pressure at a position X and Vm maximum sound pressure along the axis X. FIG. 3(c) shows that the energy distributions of beam section at positions (i) through (viii) indicated in FIG. 3(b). Xmax denotes the last position where maximum amplitude along the X axis occurs. Even for the same attenuating medium 4, therefore, the characteristics of the transmitted ultrasonic beam incident upon the medium differ depending upon the distance X from the transducer 1, as shown in FIGS. 3(a) through 3(c). The unfortunate consequence is the aforementioned problem, namely the fact that the results of measurement depend upon the characteristics of the transmitted sound field.

Attempts to solve this problem have been reported. See, for example, "Quantitative Volume Backscatter Imaging" by Matthew O'Donnell in *IEEE Transactions on Sonics and Ultrasonics*, Vol. 30, No. 1 (1983), and "A beam Corrected Estimation of the Frequency Dependent Attenuation of Biological Tissue from Backscattered Ultrasound" by M. J. T. M. Cloostermans, et. al., in *Ultrasonic Imaging*, Vol. 5, (1983). These papers describe attempts to diminish the influence of the transmitted sound field characteristics by using an echo signal received from a reference reflector to normalize an echo signal received from a object over an identical distance. A planar reflector immersed in degassed water is employed as the reference reflector. Using the planar reflector for this purpose is a more or less practical method in view of what is stated in the definition of reflective power given on page 49 of the *Handbook of Ultrasonic Technology*, published by The Nikkan Kogyo Shimbun Ltd., in which it is mentioned that the sound pressure of a wave reflected from a perfectly reflective infinite plane is taken as a standard. Nonetheless, it cannot be truely said on the basis of these reports that fully satisfactory results are obtained by a normalization method using the sound pressure of waves reflected from such a simple planar reflector in due consideration of the complicated energy distributions, as shown in FIG. 3(c). Moreover, there is still no clear solution as to what kind of reflector should best chosen as a standard reflector in the case of a highly complicated object such as biological tissue.

SUMMARY OF THE INVENTION

An object of the present invention is to provide a method and apparatus for ultrasonic measurement which solves the aforementioned problems encountered in the prior art by measuring the acoustic characteristic of a object upon minimizing the influence which the sound field characteristics of an ultrasonic wave transmitted by a transducer into the object have upon an ultrasonic wave received from the object.

According to one aspect of the present invention, the foregoing object is attained by providing an ultrasonic measurement method for measuring acoustic characteristics of a object under examination by transmitting an ultrasonic pulse into the object and detecting an ultrasonic echo signal reflected from within the object. The method includes steps of preparing a plurality of standard media having attenuation coefficients that differ from one another, transmitting ultrasonic pulses into each standard medium and then finding and storing in memory a first attenuation rate for each of a variety of different depths in each standard medium based on an ultrasonic echo signal from each depth, transmitting ultrasonic pulses having a plurality of substantially different frequency components into each standard medium and then finding and storing in memory an attenuation coefficient based on an ultrasonic signal which has passed through each standard medium, transmitting ultrasonic pulses having a plurality of different frequencies into the object, measuring a second attenuation rate over a desired range of depths in the object based on an ultrasonic echo signal received from within the object, calculating a difference between the second attenuation rate obtained with regard to the desired range of depths in the object and the first attenuation rate of a corresponding range of depths in each of the standard media, and finding the attenuation coefficient corresponding to the standard medium of which first attenuation rate gives the minimum value of the difference, this attenuation coefficient being adopted as an attenuation coefficient of the desired range of depths of the object.

According to another aspect of the present invention, the foregoing object is attained by providing an ultrasonic measurement apparatus for measuring acoustic characteristics of a object under examination by transmitting an ultrasonic pulse into the object and detecting an ultrasonic echo signal reflected from within the object. The apparatus comprises ultrasonic transceiving means for transmitting ultrasonic pulses and receiving ultrasonic signals, memory means for storing the ultrasonic signals received by the transceiving means, arithmetic means for operating on the received ultrasonic signals to find attenuation rates and differences between attenuation rates, and control means for controlling the transceiving means, the memory means and the arithmetic means, wherein in response to control executed by the control means, the transceiving means transmits ultrasonic pulses into each of a plurality of standard media having attenuation coefficients that differ from one another, the arithmetic means finds a first attenuation rate for each of a variety of different depths in each standard medium based on an ultrasonic echo signal obtained from each depth and stores it in the memory means, the transceiving means transmits ultrasonic pulses having a plurality of different frequency components into each standard medium, the arithmetic means finds an attenuation coefficient based on an ultrasonic signal which has passed through each standard medium and stores the attenuation coefficients in the memory means, the transceiving means transmits ultrasonic pulses having a plurality of different frequencies into the object, the arithmetic means finds a second attenuation rate over a desired range of depths in the object based on an ultrasonic echo signal received from within the object, the first attenuation rate of a corresponding range of depths in each of the standard media is read out of the memory means, the arithmetic means calculates a difference between the first attenuation rate read out of the memory means and the second attenuation rate obtained with regard to the desired range of depths in the object and finds the attenuation coefficient of whichever one of the standard media gives the minimum value of the difference, the attenuation coefficient being adopted as an attenuation coefficient over the desired range of depths of the object.

According to further aspect of the present invention, the foregoing object is attained by providing an ultrasonic measurement apparatus for measuring acoustic characteristics of a object under examination by transmitting an ultrasonic pulse into the object and detecting an ultrasonic echo signal reflected from within the object, said apparatus comprising:

memory means for storing an attenuation coefficient, obtained in advance, of each of a plurality of standard media having attenuation coefficients that differ from one another, and a first attenuation rate, obtained in advance, for each of a variety of depths in each of the standard media; ultrasonic transceiving means for transmitting ultrasonic pulses into and receiving ultrasonic echo signals from within the object; arithmetic means; and control means for controlling said transceiving means, said memory means and said arithmetic means, wherein in response to control executed by said control means, said transceiving means transmits ultrasonic pulses having a plurality of different frequency components into the object, said arithmetic means finds a second attenuation rate over a desired range of depths in the object based on ultrasonic echo signals received from within the object, the first attenuation rate over a range of depths in each of the standard media corresponding to the range of depths in the object is read out of said memory means, said arithmetic means calculates a difference between each of the first attenuation rates read out of said memory means and the attenuation rate obtained with regard to the desired range of depths in the object and finds the standard medium corresponding to the first attenuation rate that gives the minimum value of said difference, and characterized in that said first attenuation coefficient is adopted as an attenuation coefficient over the desired range of depths of the object.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 1, 2 and 3(a) through 3(c) are views useful in describing a method of ultrasonic measurement according to the prior art;

FIGS. 9(a) through 9(c) are views for describing an ultrasonic measurement operation performed by the apparatus embodied in FIG. 8;

FIG. 11 is a view showing an example of a data storage format in a standard data memory of the apparatus shown in FIG. 8;

DESCRIPTION OF THE PREFERRED EMBODIMENT

Figure 3:
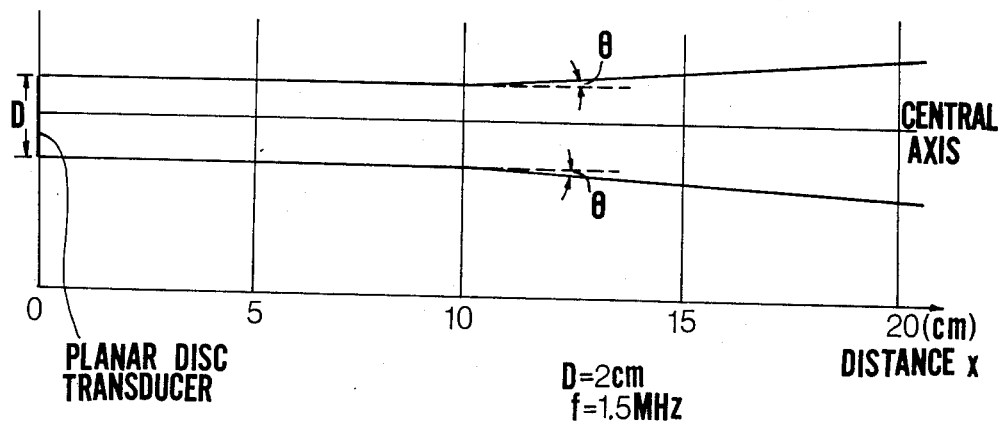
Figure 3:
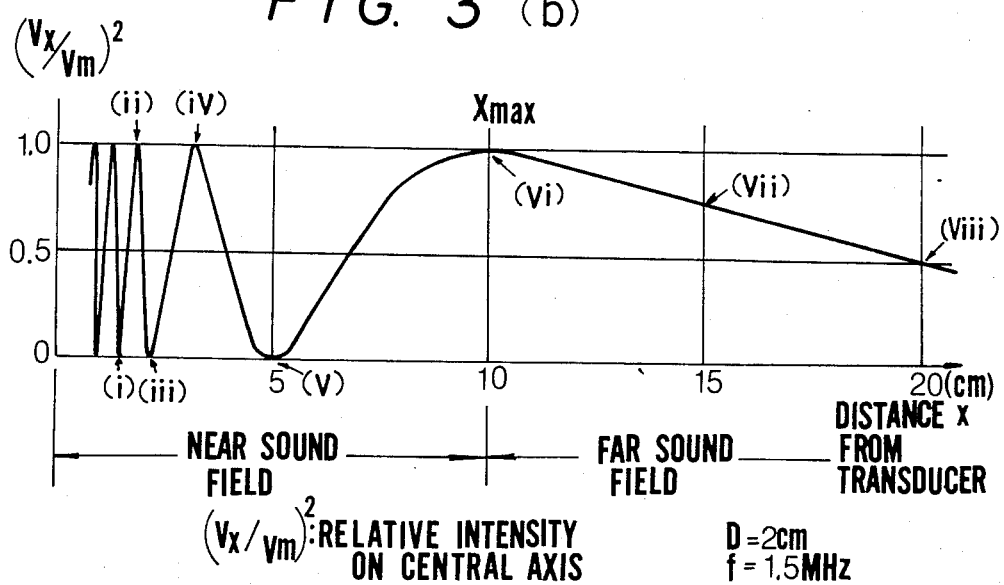
Figure 3:
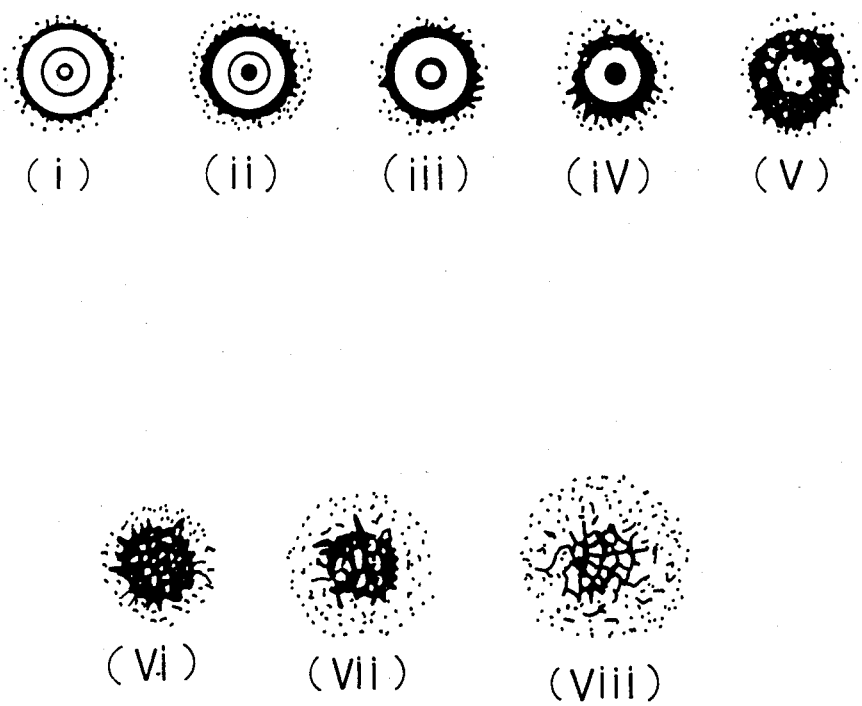
Figure 4:
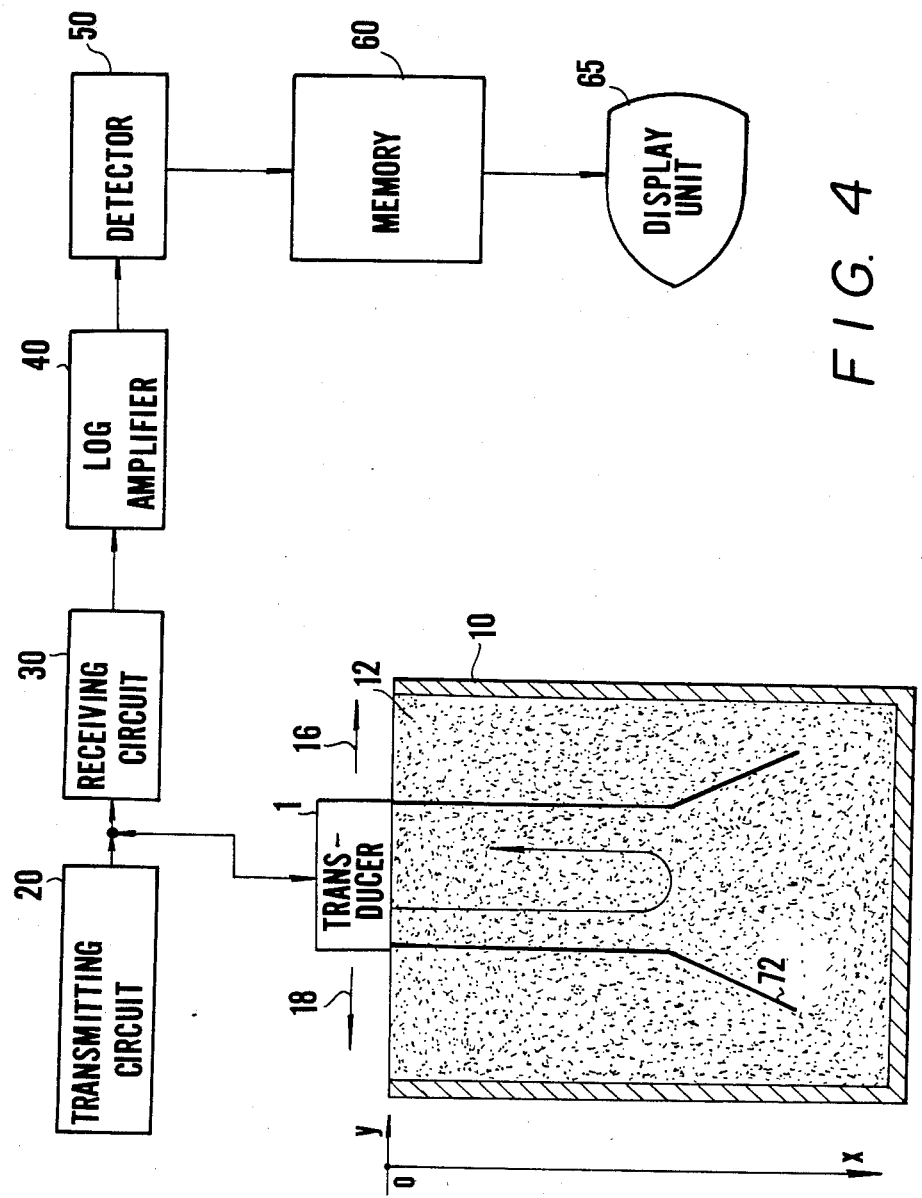
FIG. 4 is a functional block diagram for describing the principle of a method of ultrasonic measurement according to the present invention.

A preferred embodiment of the present invention will now be described in detail, starting with a discussion of the principle of the invention with reference to FIG. 4.

A vessel 10 is filled with a medium 12 which exhibits a uniform attenuation with respect to ultrasonic waves. The medium 12 is so prepared as to have an attenuation coefficient substantially the same as the mean attenuation coefficient of soft biological tissue, namely 1 dB/cm MHz, and an acoustic impedence substantially the same as the mean acoustic impedence of a living body, namely $1.5 \times 10^6$ kg/m$^2$ s, and so that the velocity of sound within the medium will be substantially the same as the mean sonic velocity in a living body, namely 1500 m/s. In a word, the medium 12 is a so-called phantom approximating a living body. Methods of preparing such a phantom have been reported in, for example, "Oil-in-Gelatin Dispersions for use as Ultrasonically Tissue-Mimicking Materials" by Ernest L. Madsen in *Ultrasound in Medicine and Biology*, Vol. 8, No. 3 (1982) and "Tissue Mimicking Materials for Ultrasound Phantoms" by Ernest L. Madsen in *Medical Physics*, Vol. 5, No. 5 (1978).

Figure 6:
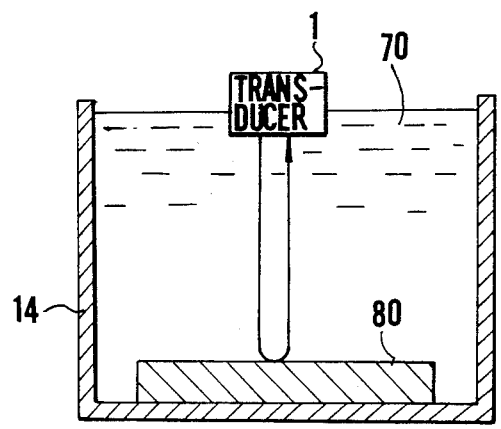
Figure 6:
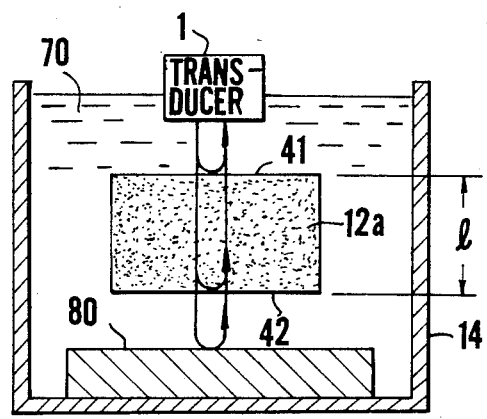
Figure 6:
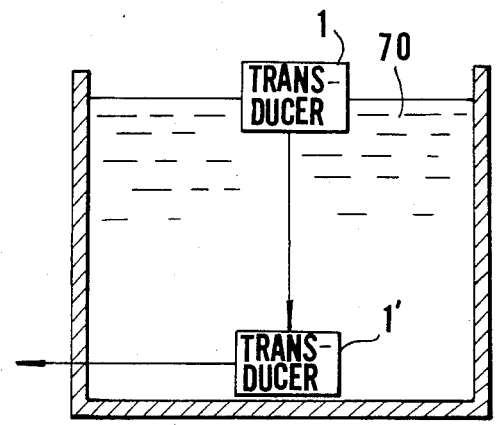
Figure 6:
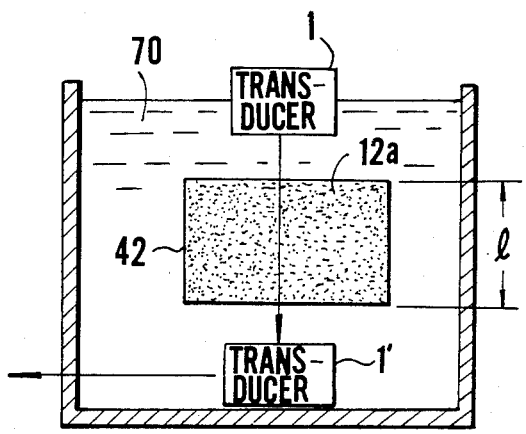

The various acoustic parameters of a phantom (the uniformly attenuating medium 12) thus prepared are capable of being measured in advance. Specifically, the attenuation coefficient can be measured by a so-called transmission-reflection method as illustrated in (a) and (b) of FIG. 6, or by a so-called transmission method as depicted in (c) and (d) of FIG. 6. In FIG. 6(a), a perfect reflector 80 is immersed in degassed water 70 contained by a vessel 14. The amplitude Vo(f) of an echo received by the transducer 1 from the perfect reflector 80 is measured. A phantom 12a made of the same material at the above-described attenuating medium 12 and having front and back sides 41, 42, respectively, is then immersed in the degassed water 70 and disposed between the transducer 1 and the perfect reflector 80, as shown in FIG. 6(b). The amplitude V(f) of an echo received by the transducer 1 from the perfect reflector 80 is now measured under exactly the same conditions that prevailed in FIG. 6(a), the only difference being the presence of the phantom 12a. With such an arrangement, the mean value αo of the attenuation coefficient of the phantom 12a can be found from the following equation:

$$\alpha o = \ln[Vo(f)/V(f)]/2l \cdot f$$

where l is the thickness of the phantom 12a and $\alpha(f) = \alpha o \cdot f$. Further, $$\alpha o = \int_0^l \alpha o(X) dX.$$

Next, mean propagation velocity C of sound within the phantom in FIG. 6(b) is found from times $t_{41}$, $t_{42}$ required to receive echos from the front and back surfaces 41, 42 of the phantom 12a, respectively. C is found from the following equation:

$$C = 2l/(t_{42} - t_{41})$$

The acoustic impedance Z of the phantom 12a is found from the product of the propagation velocity C of sound and the density ρ of the phantom 12a, i.e., Z=ρC.

In FIG. 6(c), the vessel 14 is filled with degassed water 70. Instead of the perfect reflector 80, a transducer 1' solely for reception purposes is immersed in the degassed water 70 directly opposite the transducer 1, which is solely for transmission. The transducer 1 emits an ultrasonic wave which is received by the transducer 1'. Let $V_T^o(f)$ represent the amplitude of the received ultrasonic wave. The phantom 12a made of the same material as the attenuating medium 12 is then immersed in the degassed water 70 and disposed between the transducers 1, 1', as shown in FIG. 6(d). The amplitude $V_T(f)$ of the ultrasonic wave received by the transducer 1' from the transducer 1 upon passing through the phantom 42 is now measured under exactly the same conditions that prevailed in FIG. 6(c), the only difference being the presence of the phantom 12a. With such an arrangement, the means value αo of the attenuation coefficient of the phantom 12a can be found from the following equation:

$$\alpha o = \ln(V_T^o(f)/V_T(f))/l \cdot f$$

where $$\alpha o = \int_0^l \alpha o(X) dX$$

Thus, forming the medium 12 into a phantom of which acoustic characteristics is nealy that of soft biological tissue and both measuring and confirming the characteristics of the medium can be achieved by using presently available techniques.

Let us return to FIG. 4 to investigate the results of measuring the medium 12 using the conventional pulse echo method. Part of FIG. 4 shows a block diagram constituting a B-mode scanner section which operates on the basis of the conventional pulse echo method. A transmitting circuit 20 applies a pulsed drive voltage to the transducer 1, which responds by transmitting an ultrasonic wave 72 into the medium 12. The transducer 1 receives an echo from the medium 12 and applies the echo signal to a receiving circuit 30. The receiving circuit 30 applies the signal to a logarithmic amplifier 40 where the signal is logarithmically amplified into an output signal applied to a detector 50. The output of the detector 50 is stored in a memory 60 and is displayed as a B-mode image on a display unit 65. The transducer 1 is scanned by a scanner (not shown) in the Y direction as indicated by the arrows 16, 18, with the timing of the overall operation being controlled by a control circuit, not shown.

At any given position, an A-mode signal output V(f,X), namely the input to the receiving circuit 30, should be given by the following equation, in which X represents the depth of the medium 12:

$$V(f, X) = Vo(f) \cdot R(f, X) \cdot \exp\left\{-2 \int_0^X \alpha(f, X)dX\right\} \quad (1)$$

Here R(f,X) represents the reflector strength. Taking the natural logarithm of both sides of Eq. (1) and transforming results in the following equation:

$$\ln V(f, X) = \ln Vo(f) + \ln R(f, X) - 2 \int_0^X \alpha(f, X)dX \quad (2)$$

Assuming that $\alpha(f,X) = \alpha o(X) \cdot f$ holds, we have $$\int_0^X \alpha(f, X)dX = f \cdot \overline{\alpha o} \cdot X.$$

It is assumed that $$\frac{\partial}{\partial X} \alpha o(X) \simeq 0,$$

namely that $$\int_0^X \alpha o(X)dX = \overline{\alpha o} \int_0^X dX = \overline{\alpha o} \cdot X.$$

It is also assumed that $$\frac{\partial}{\partial X} R(f, x) = 0$$

holds, namely that R(f,x) is uniform in the medium 12. Thus, we arrive at the following equation:

$$\ln V(f,X) = \ln Vo(f) + \ln R(f) - 2\overline{\alpha o} \cdot f \cdot X \quad (3)$$

Figure 5:
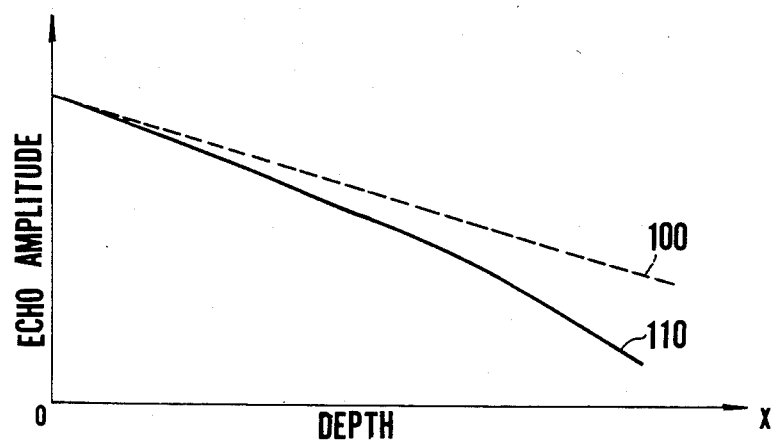
FIGS. 5 through 7 are views for describing the fundamental principle of the present invention.

The first and second terms on the right side of Eq. (3) are constants independent of depth X. Therefore, it depth X is plotted along the horizontal axis and the echo amplitude lnV(f,X) along the vertical axis, as shown in FIG. 5, one would expect the measured echo amplitude to decrease linearly as shown by curve 100 at a constant frequency f. As set forth earlier, however, the beam shape of the transmitted sound field is dependent upon the depth X and varies as shown at 72 in FIG. 4. Accordingly, the amplitude of the echo received by the transducer 1 is weakened owing to diffusion of the beam. As a result, it may be presumed that the echo amplitude lnV(f,X) will attenuate with depth X, as shown by the solid line 110 in FIG. 5, to a greater extent than indicated by the dashed line 100 that represents an ideal case.

Measured acoustic characteristics are influenced by this beam diffusion phenomenon ascribable to the transmitted sound field characteristics even where the object is biological tissue. If a transmitted sound field could be actually measured by some method or theoretically analyzed in advance, then it would be possible to correct for the transmitted sound field characteristics and obtain acoustic characteristics improved quantitatively. In actuality, however, a technique of this kind has not yet be established and the above-described method of transmitted sound field correction based on a standard planar reflector represents the present technical level.

An object of the present invention is to provide an ultrasonic measurement method and apparatus wherein a B-mode image is obtained by the transducer 1 from the medium 12, which is considered to be one standard medium, a B-mode image is obtained from biological tissue by using the same transducer 1, the two B-mode images are compared and the influence of the characteristics of the sound field transmission from the transducer 1 is reduced.

Let us now describe one known measurement method for finding an attenuation coefficient of a object by using the pulse echo technique.

Figure 7:
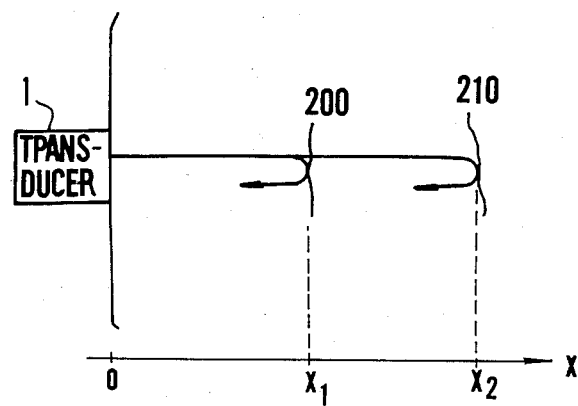

As shown in FIG. 7, two reflectors 200, 210 are disposed at respective distances of $X_1$, $X_2$ from the transducer 1, which receives pulse echos of amplitude $V(f,X_1)$, $V(f,X_2)$ from the reflectors 200, 210, respectively. The pulse echo amplitudes $V(f,X_1)$, $V(f,X_2)$ are given by the following equations:

$$V(f, X_1) = Vo(f) \cdot R(f, X_1) \cdot \exp\left\{-2 \int_0^{X_1} \alpha(f, X)dX\right\} \quad (4)$$

$$V(f, X_2) = Vo(f) \cdot R(f, X_2) \cdot \exp\left\{-2 \int_0^{X_2} \alpha(f, X)dX\right\} \quad (5)$$

Taking the natural logarithm of both side of Eqs. (4), (5) and transforming gives the following:

$$\ln[V(f, X_1)/Vo(f)] = \ln[R(f, X_1)] - 2 \int_0^{X_1} \alpha(f, X)dX \quad (6)$$

$$\ln[V(f, X_2)/Vo(f)] = \ln[R(f, X_2)] - 2 \int_0^{X_2} \alpha(f, X)dX \quad (7)$$

Subtracting Eq. (7) from Eq. (6), we have:

$$\ln[V(f, X_1)/V(f, X_2)] = \ln[R(f, X_1)/R(f, X_2)] + 2 \int_{X_1}^{X_2} \alpha(f, X)dX \quad (8)$$

$$\therefore \int_{X_1}^{X_2} \alpha(f, X)dX = \tfrac{1}{2}\ln[V(f, X_1)/V(f, X_2)] - \tfrac{1}{2}\ln[R(f, X_1)/R(f, X_2)] \quad (9)$$

Since $\alpha(f,X) = \alpha o(X) \cdot f$ will hold for soft biological tissue, we may write the following:

$$\int_{X_1}^{X_2} \alpha(f, X)dX = f \cdot \int_{X_1}^{X_2} \alpha o(X)dX =$$

$$f \cdot \overline{\alpha o} \int_{X_1}^{X_2} dX = f \cdot \overline{\alpha o}(X_2 - X_1)$$

where $\overline{\alpha o}$ is the mean attenuation coefficient in the interval between $X_1$ and $X_2$. FIG. 9 permits $\overline{\alpha o}$ to be expressed by the following equation:

$$\overline{\alpha_o} = \frac{1}{2f(X_2 - X_1)} \{\ln[V(f, X_1)/V(f, X_2)] - \ln[R(f, X_1)/R(f, X_2)]\} \quad (10)$$

The second term on the right side of Eq. (10) represents the ratio of the reflector strength of the echo from reflector 200 at $X_1$ to the reflector strength of the echo from the reflector 210 at $X_2$. If the reflector strengths are equal, namely if $R(f,X_1)/R(f,X_2) \simeq 1$ holds, then the second term on the right side of Eq. (10) will approximate zero and the mean value $\overline{\alpha}$ of the attenuation coefficient can be measured with generally good accuracy.

If the measurement is made using two different frequencies $f_1$, $f_2$, Eq. (8) will yield the following two equations, one for $f_1$ and one for $f_2$:

$$\ln[V(f_1, X_1)/V(f_1, X_2)] = \ln[R(f_1, X_1)/R(f_1, X_2)] + \quad (11)$$
$$2 \int_{X_1}^{X_2} \alpha(f_1, X)dX$$

$$\ln[V(f_2, X_1)/V(f_2, X_2)] = \ln[R(f_2, X_1)/R(f_2, X_2)] + \quad (12)$$
$$2 \int_{X_1}^{X_2} \alpha(f_2, X)dX$$

Subtracting Eq. (11) from Eq. (12) gives the following equation:

$$\ln\left[\frac{V(f_2, X_1)}{V(f_2, X_2)} / \frac{V(f_1, X_1)}{V(f_1, X_2)}\right] = \ln\left[\frac{R(f_2, X_1)}{R(f_2, X_2)} / \frac{R(f_1, X_1)}{R(f_1, X_2)}\right] + \quad (13)$$
$$2 \int_{X_1}^{X_2} [\alpha(f_2, X) - \alpha(f_1, X)]dX$$

From $\alpha(f,X) = \alpha_o(X) \cdot f$, we obtain the following:

$$\int_{X_1}^{X_2} [\alpha(f_2, X) - \alpha(f_1, X)]dX = (f_2 - f_1)\overline{\alpha_o}(X_2 - X_1) \quad (13')$$

We therefore have the following equation:

$$\overline{\alpha_o} = \frac{1}{2(f_2 - f_1) \cdot (X_2 - X_1)} \left\{ \ln\left[\frac{V(f_2, X_1)}{V(f_2, X_2)} / \frac{V(f_1, X_1)}{V(f_1, X_2)}\right] - \ln\left[\frac{R(f_2, X_1)}{R(f_2, X_2)} / \frac{R(f_1, X_1)}{R(f_1, X_2)}\right] \right\} \quad (14)$$

If the reflector strengths are about the same, namely if $$\left[\frac{R(f_2, X_1)}{R(f_1, X_1)} / \frac{R(f_2, X_2)}{R(f_1, X_2)}\right] \simeq 1,$$

then the second term on the right side of Eq. (14) will approximate zero and $\alpha_o$ can be found from the following equation:

$$\overline{\alpha_o} = \frac{1}{2(f_2 - f_1)(X_2 - X_1)} \cdot \left\{ \ln\left(\frac{V(f_2, X_1)}{V(f_2, X_2)} / \frac{V(f_1, X_1)}{V(f_1, X_2)}\right) \right\} \quad (15)$$

As set forth above, however, the measured value ln V(f,x) apparently decreases with distance X, as shown by the curve 110 in FIG. 5, owing to diffusion of the transmitted beam 72. This results in a problem wherein the attenuation coefficient measured appears larger with distance X than in actuality. Moreover, one must also take into consideration the influence of the fact that the reflected wave arrives at the transducer 1 while diffusing spatially.

Taking the foregoing points into consideration, we apply a correction to the fundamental equation (1) and arrive at the following:

$$V(f, X) = Vo(f) \cdot G(f, X) \cdot R(f, X) \cdot D(f, X) \cdot \quad (16)$$
$$\exp\left\{-2 \int_o^X \alpha(f, X)dX\right\}$$

where G(f,X), D(f,X) are diffusion terms that take into account the diffusion of the transmitted beam 72 and the diffusion of the reflected wave, respectively.

On the basis of the foregoing, Eq. (9) is corrected as follows:

$$2 \int_{X_1}^{X_2} \alpha(f, X)dX = \ln[V(f, X_1)/V(f, X_2)] - \quad (17)$$
$$\ln[G(f, X_1)/G(f, X_2)] - \ln[R(f, X_1)/R(f, X_2)] -$$
$$\ln[D(f, X_1)/D(f, X_2)]$$

The second term on the right side of Eq. (17) is an error term ascribable to the transmitted sound field, though the term will approximate zero if G(f,X) is constant and independent of depth (distance) X. Since the transmitted sound field varies in a complex manner as described above, however, G(f,X) may be presumed to vary with distance X. Assume now that the echo from the standard medium 12 is expressed by Vs(f,X). At the transducer 1, therefore, Vs(f,Xs) may be expressed as follows:

$$Vs(f, Xs) = Vo(f) \cdot Gs(f, Xs) \cdot Rs(f, Xs) \cdot Ds(f, Xs) \cdot \quad (18)$$
$$\exp\left\{-2 \int_o^{Xs} \alpha s(f, Xs)dXs\right\}$$

Normalizing Eq. (16) by Eq. (18) results in the following:

$$V(f, X)/Vs(f, Xs) = [G(f, X)/Gs(f, Xs)] \cdot [R(f, X)/Rs(f, Xs)] \cdot [D(f, X)/Ds(f, Xs)] \cdot \quad (19)$$

$$\left[\exp\left\{-2\int_0^X \alpha(f,X)dX\right\}\right] / \left[\exp\left\{-2\int_0^{X_s} \alpha s(f,X s)dX s\right\}\right]$$

In Eq. (19), X and Xs are equal to C·t and Cs·t, respectively, where C is the mean velocity of sound in biological tissue and Cs is the mean velocity of sound in the standard medium 12.

If the standard medium 12 is so prepared that the mean sonic velocity Cs therein is equal to the mean sonic velocity C in the biological tissue, i.e., so that Cs=C holds, as mentioned earlier, then X=Xs will hold. Accordingly, taking the natural logarithm of both sides of Eq. (19) and transforming results in the following equation:

$$\ln[V(f,X)/Vs(f,X)] = \ln[G(f,X)/Gs(f,X)] + \tag{20}$$

$$\ln[R(f,X)/Rs(f,X)] + \ln[D(f,X)/Ds(f,X)] + 2\int_0^X [\alpha s(f,X) - \alpha(f,X)]dX$$

In the manner set forth above, pulse echo amplitudes $V(f,X_1)$, $V(f,X_2)$ for the two distances $X_1$, $X_2$, respectively, are measured, and the difference between the two amplitudes is calculated. The following equation is obtained:

$$\ln\left(\frac{V(f,X_1)}{Vs(f,X_1)} \Big/ \frac{V(f,X_2)}{Vs(f,X_2)}\right) = \ln\left(\frac{G(f,X_1)}{Gs(f,X_1)} \Big/ \frac{G(f,X_2)}{Gs(f,X_2)}\right) + \tag{21}$$

$$\ln\left(\frac{R(f,X_1)}{Rs(f,X_1)} \Big/ \frac{R(f,X_2)}{Rs(f,X_2)}\right) +$$

$$\ln\left(\frac{D(f,X_1)}{Ds(f,X_1)} \Big/ \frac{D(f,X_2)}{Ds(f,X_2)}\right) + 2\int_{X_1}^{X_2} [\alpha s(f,X) - \alpha(f,X)]dX$$

The second term on the right side of Eq. (21) approximates zero if we consider that $R(f,X_1)/R(f,X_2)\approx 1$ holds, as mentioned above. The first term, which is a diffusion term ascribable to the transmitted sound field, is normalized by the standard medium 12 and is thus predicted to have a value which is negligibly small. Accordingly, Eq. (21) can be approximated as follows:

$$\ln\left(\frac{V(f,X_1)}{Vs(f,X_1)} \Big/ \frac{V(f,X_2)}{Vs(f,X_2)}\right) \approx \tag{22}$$

$$\ln\left(\frac{D(f,X_1)}{Ds(f,X_1)} \Big/ \frac{D(f,X_2)}{Ds(f,X_2)}\right) + 2\int_{X_1}^{X_2} [\alpha s(f,X) - \alpha(f,X)]dX$$

We may define a relative attenuation coefficient A based on the standard medium 12 in the interval between $X_1$ and $X_2$ as follows:

$$A \equiv \ln\left(\frac{V(f,X_1)}{Vs(f,X_1)} \Big/ \frac{V(f,X_2)}{Vs(f,X_2)}\right)$$

Therefore, if a coefficient of attenuation of a object is near that of the standard medium 12, i.e., if the relation $\alpha(f,X)\approx\alpha s(f,X)$ holds, then the second term on the right side of Eq. (22) will approximate zero.

This leaves the the first term on the right side of Eq. (22), namely the term that takes into account the diffusion of the reflected wave. However, considering that $D(f,x)=X^{b(x)}$, as has already been reported, b(X) will be zero for a scatterer of a size which is large in comparison with the wavelength of the ultrasonic wave, and −1 for a scatterer of a size small in comparison with the ultrasonic wavelength. Furthermore, this relation may be considered to be constant within the range of wavelengths or frequencies used.

Accordingly, if we write Eq. (22) for the two different frequencies $f_1$, $f_2$ by using Eq. (13), we have the following:

$$\ln\left\{\left(\frac{V(f_2,X_1)}{Vs(f_2,X_1)} \Big/ \frac{V(f_2,X_2)}{Vs(f_2,X_2)}\right) \Big/ \left(\frac{V(f_1,X_1)}{Vs(f_1,X_1)} \Big/ \frac{V(f_1,X_2)}{Vs(f_1,X_2)}\right)\right\} \approx \tag{23}$$

$$\ln\left\{\left(\frac{D(f_2,X_1)}{Ds(f_2,X_1)} \Big/ \frac{D(f_2,X_2)}{Ds(f_2,X_2)}\right) \Big/ \left(\frac{D(f_1,X_1)}{Ds(f_1,X_1)} \Big/ \frac{D(f_1,X_2)}{Ds(f_1,X_2)}\right)\right\} + 2\int_{X_1}^{X_2}\{[\alpha s(f_2,X) - \alpha(f_2,X)] -$$

$$[\alpha s(f_1,X) - \alpha(f_1,X)]\}dX$$

From the relation $D(f_1,X)\approx D(f_2,X)$, the first term on the right side of Eq. (23) approximates zero, so that Eq. (23) can be approximated by the following equation:

$$\ln\left(\left[\frac{V(f_2,X_1)}{Vs(f_2,X_1)} \Big/ \frac{V(f_2,X_2)}{Vs(f_2,X_2)}\right] \Big/ \left[\frac{V(f_1,X_1)}{Vs(f_1,X_1)} \Big/ \frac{V(f_1,X_2)}{Vs(f_1,X_2)}\right]\right) \approx \tag{24}$$

$$2\int_{X_1}^{X_2}\{[\alpha s(f_2,X) - \alpha(f_2,X)] - [\alpha s(f_1,X) - \alpha(f_1,X)]\}dX =$$

$$2\int_{X_1}^{X_2}\{[\alpha s(f_2,X) - \alpha s(f_1,X)] - [\alpha(f_2,X) - \alpha(f_1,X)]\}dX$$

Therefore, the measured quantity on the left side of Eq. (24), namely a quantity obtained by normalizing the pulse echo amplitudes $V(f_1,X_1)$, $V(f_2,X_1)$, $V(f_1,X_2)$, $V(f_2,X_2)$ for the object at the two different distances (depths) $X_1$, $X_2$ for the two different frequencies by the corresponding pulse echo amplitudes $Vs(f_1, X_1)$, $Vs(f_2,$ $X_1$), $V_s(f_1, X_2)$, $V_s(f_2, X_2)$ for the standard medium 12, gives the difference between the attenuation coefficients $\alpha_s(f_2,X)$, $\alpha_s(f_1,X)$ of the standard medium 12 at the frequencies $f_1$, $f_2$ on the right side of Eq. (24). Accordingly, if the attenuation coefficients $\alpha(f_2,X)$, $\alpha(f_1,X)$ of the object at the frequencies $f_1$, $F_2$ nearly equal to the corresponding attenuation coefficients values of the standard medium 12, then the measured quantity (the left side of Eq. (24)) will approximate zero.

Utilizing this theory makes it possible to measure, in approximate terms, the frequency dependence of the attenuation coefficient of the object. Let us describe this in greater detail.

A plurality of standard media each having a different attenuation coefficient $\alpha_s(f)$ which are known are prepared in advance, the pulse echo amplitudes $V_s(f,X)$ of each medium at various distance are measured in advance, and the amplitudes $V_s(f,x)$ and each attenuation coefficients $\alpha_s(f)$ are stored in memory at the same time. Next, the pulse echo amplitude $V(f,X)$ of the object is measured, the left side of Eq. (24) is calculated and a value of $V_s(f,X)$ is found that will cause the value of the left side of the equation to approximate zero. The corresponding $\alpha_s(f)$ is then fetched from memory and this value (attenuation coefficient) is defined as being the attenuation coefficient of the object. Through this method, use of the standard media makes it possible to measure the attenuation coefficient of the object while diminishing the influence of the sound field of the ultrasonic wave transmitted by the transducer used in making the measurement.

To make the above discussion clearer, transforming Eq. (24) results in the following equation:

$$\ln\left[\frac{V(f_2,X_1)}{V(f_2,X_2)} \Big/ \frac{V(f_1,X_1)}{V(f_1,X_2)}\right] - \ln\left[\frac{V_s(f_2,X_1)}{V_s(f_2,X_2)} \Big/ \frac{V_s(f_1,X_1)}{V_s(f_1,X_2)}\right] \approx \quad (25)$$

$$2\int_{X_1}^{X_2}[\{\alpha_s(f_2,X) - \alpha_s(f_1,X)\} - \{\alpha(f_2,X) - \alpha(f_1,X)\}]dX$$

Eq. (25) has the following form:

$$W(f_1,f_2)x_1,x_2 - W_s(f_1,f_2)x_1,x_2 = \Delta\alpha_s(f_1,f_2) - \Delta\alpha(f_1,f_2) \quad (26)$$

where $$W(f_1,f_2)x_1,x_2 = \quad (27)$$

$$\frac{1}{2(X_2 - X_1)\cdot(f_2 - f_1)}\cdot\ln\left[\frac{V(f_2,X_1)}{V(f_2,X_2)} \Big/ \frac{V(f_1,X_1)}{V(f_1,X_2)}\right]$$

$$W_s(f_1,f_2)x_1,x_2 = \quad (28)$$

$$\frac{1}{2(X_2 - X_1)\cdot(f_2 - f_1)}\cdot\ln\left[\frac{V_s(f_2,X_1)}{V_s(f_2,X_2)} \Big/ \frac{V_s(f_1,X_1)}{V_s(f_1,X_2)}\right]$$

$$\Delta\alpha_s(f_1,f_2) = \frac{1}{(X_2 - X_1)\cdot(f_2 - f_1)}\int_{X_1}^{X_2}[\alpha_s(f_2,X) - \alpha_s(f_1,X)]dX \quad (29)$$

$$\Delta\alpha(f_1,f_2) = \frac{1}{(X_2 - X_1)\cdot(f_2 - f_1)}\int_{X_1}^{X_2}[\alpha(f_2,X) - \alpha(f_1,X)]dX \quad (30)$$

Accordingly, we can say that it is possible to find a standard medium where the measured quantity $W(f_1,f_2)x_1,x_2$ nearly equals to the known quantity $W_s(f_1,f_2)x_1,x_2$ at the frequencies $f_1$, $f_2$, and the sought attenuation coefficient $\Delta\alpha(f_1,f_2)$ between distance $x_1$ and $x_2$ can be considered to be the known attenuation coefficient $\Delta\alpha_s(f_1,f_2)$. We may designate $W(f_1,F_2)x_1,x_2$ as an attenuation rate between $x_1$ and $x_2$ for the object, and $W_s(f_1,f_2)x_1,x_2$ as an attenuation rate for the standard media, hereinafter.

The ultrasonic measurement method of the present invention will be described in greater detail with reference to FIG. 8, in which the portion 2000 enclosed by the dashed line is a block having particular relevance to the present invention. The other blocks represent known art corresponding to the conventional pulse echo B-mode scanner system and therefore need not be described in detail here.

The transducer 1 set at the surface of a object 400 undergoing measurement is scanned on the surface in a direction Y at right angles to object depth X by a scanner 500. Connected to the transducer 1 are the transmitting circuit 20 and the receiving circuit 30 both of which are under the control of a control unit 1402, the former for transmitting ultrasonic waves via the transducer 1 and the latter for receiving echos reflected from the interior of the object 400.

A received echo signal is amplified by the logarithmic amplifier 40 and detected by the detector 50. The output of the detector 50 is subjected to a so-called STC correction by an STC circuit 1000. The corrected signal is stored in an image memory 1100 in the form of a digital signal. The echo data stored in the memory 1100 is amplified by a video amplifier 1200 and supplied as a video signal to a display unit 1300. The display unit 1300 may in one example include a CRT display device for displaying the measured echo data as a so-called B-mode image.

The block 2000 includes two memories, namely an echo data memory 2400 and a standard data memory 2300, as well as an arithmetic unit 2200 and a region-of-interest (ROI) setting unit 2100. As will be described below, the echo data memory 2400 is a storage area for storing, in the form of digital data, the echo signal received by the receiving circuit 30. The arithmetic unit 2200 has an arithmetic function for calculating acoustic characteristics such as the attenuation coefficients of the standard medium 12 and object 400 in accordance with the above-described principle of the present invention. Values of the attenuation rate and the attenuation coefficients for the standard medium 12 calculated by the arithmetic unit 2200 are stored in the standard data memory. These attenuation rates and attenuation coefficients for the standard medium 12 may also be calculated and stored in the standard data memory 2300 (consists of e.g. read only memory or magnetic storage device) as non-volatile data in advance of the apparatus being used for measuring acoustic characteristics of the object.

The ROI setting unit 2100 is a device manipulated by the operator to set a region of interest, namely a region in which the acoustic characteristics in particular are desired to be measured, in the B-mode echo image of the object 400 displayed on the display unit 1300. In order that a region of interest may be specified, the apparatus includes a freeze switch 1400 for freezing the echo image at a desired instant.

Figure 8:
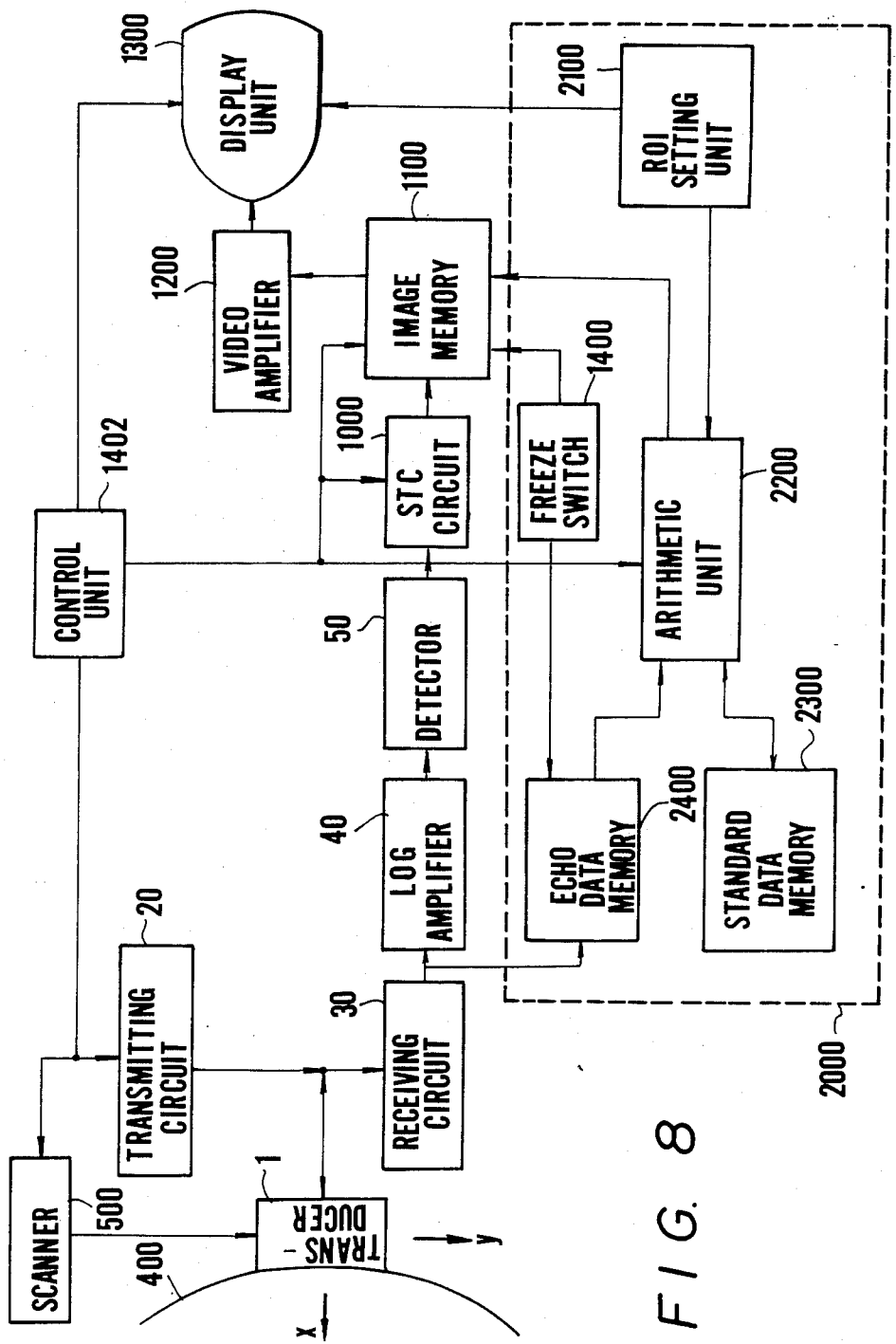
FIG. 8 is a block diagram illustrating an embodiment of an ultrasonic measurement apparatus according to the present invention.
Figure 10:
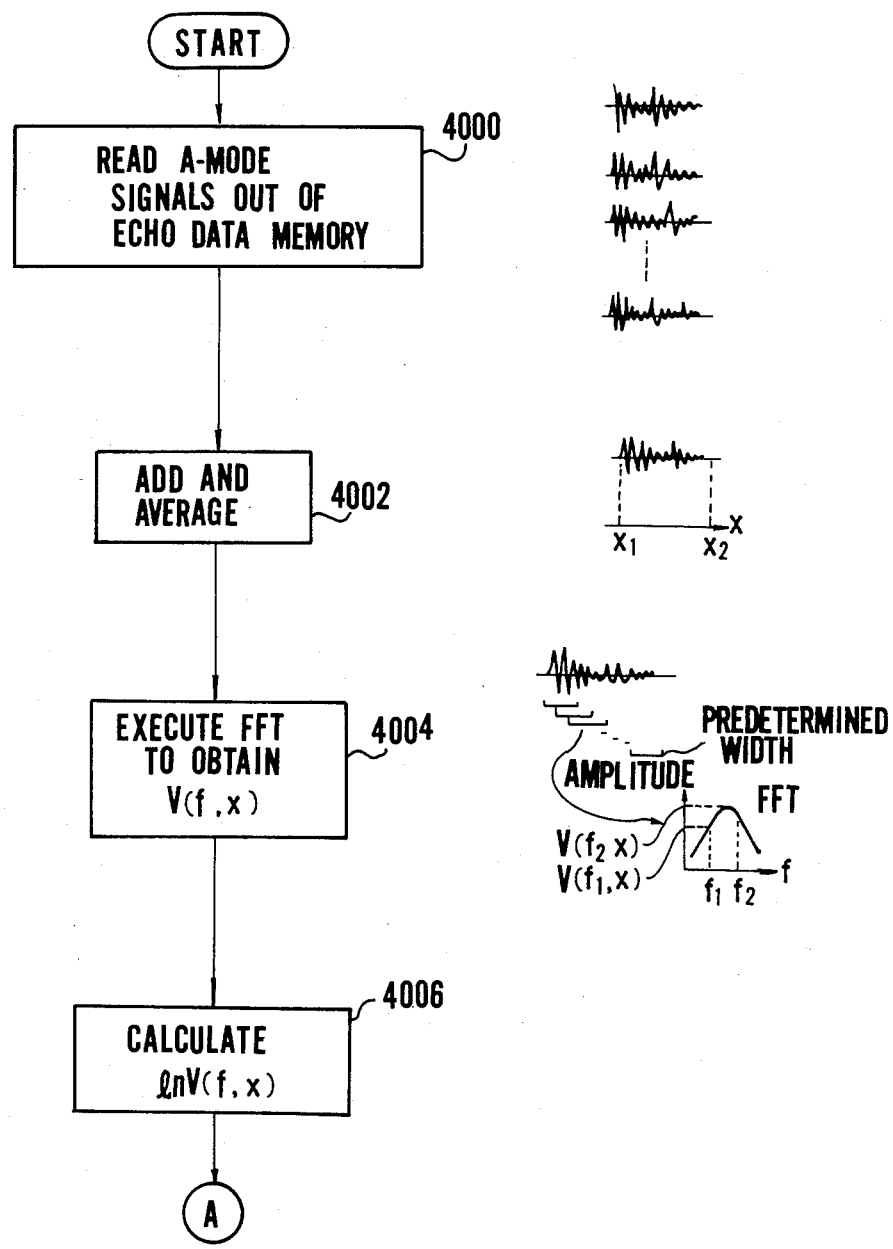
FIGS. 10(a) and 10(b) are flowcharts illustrating the operation of the apparatus of FIG. 8.

According to the embodiment of the present invention, a plurality of standard media (three in the illustrated embodiment to give a better understanding) 12b, 12c, 12d shown respectively in (a), (b) and (c) of FIG. 9 and having attenuation coefficients $\alpha s_1(f)$, $\alpha s_2(f)$ and $\alpha s_3(f)$ that differ from one another are measured in advance by using the apparatus of FIG. 8. In accordance with a processing flow similar to that of the step 4000 through 4012 in the flowcharts of FIGS. 10(a) and 10(b), $Ws_i(f_1,f_2)$ (where i=1, 2, 3) is calculated by the arithmetic unit 2200 and stored in the standard data memory 2300. It should be noted that while the flowcharts of FIGS. 10(a) through 10(b) are for the purpose of finding an attenuation coefficient regarding a measured region 3000 of a object shown in FIG. 12, the flowcharts can be applied similarly with regard to the measurement of the standard media 12b, 12c, 12d of FIG. 9 and to the calibration method shown in FIG. 6.

Echos are measured by applying the method described above with reference to FIGS. 6(a) through 6(d) to the apparatus shown in FIG. 8, $\Delta\alpha s(f_1,f_2)$ is found by the arithmetic unit 2200 on the basis of the measured echos, and the value of $\Delta\alpha s(f_1,f_2)$ is stored in the standard data memory 2300. In order to correlate $Ws_i(f_1,f_2)$ and $\Delta\alpha s_i(f_1,f_2)$ (where i is 1, 2 and 3 for the respective standard media 12b, 12c, 12d in the illustrated embodiment), the standard data are stored in the standard data memory 2300 in the form shown in FIG. 11. To make the discussion clearer, the expression $Ws_i(f_1,f_2)x_1,x_2$ are replaced by $Ws_i(f_1,f_2)_k$ in FIG. 11. Suffix k is the number indicative of distance X, and the length between k and k+1 is $\Delta X$ for any k. Specifically, taking the standard medium 12b (the attenuation coefficient of which has a frequency dependence $\Delta\alpha s_1$) as an example, there is stored the difference (see Eq. (28)) between an attenuation coefficient of an echo amplitude at the frequency $f_1$ and an attenuation coefficient of an echo amplitude at the frequency $f_2$ over each unit interval $\Delta X$, with the measurements being made by the pulse echo method.

Described next will be a method of finding the attenuation coefficient of the object 400 in accordance with the principle of the present invention. The measurement operation is executed under the control of the control unit 1402.

Figure 12:
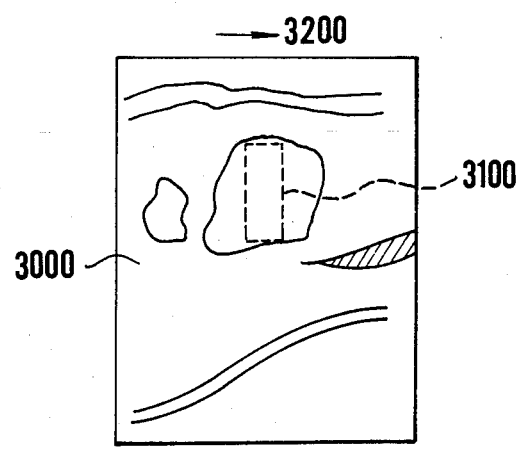
FIG. 12 is a view illustrating an example of a B-mode image of a region of interest displayed on a display unit of the apparatus shown in FIG. 8.

First, using the method of the prior art, a B-mode tomograph of the object 400 is obtained by way of the receiving circuit 30, image memory 1100 and display unit 1300 of the apparatus shown in FIG. 8. As a result, a tomograph 3000 of the kind shown in FIG. 12 is displayed on the display unit 1300. For observation purposes, the usual practice is to operate the freeze switch 1400 to display the tomograph 3000 in the form of a frozen image obtained as an output from the image memory 1100. The operator manipulates the ROI setting unit 2100 to set, on the image 3000 shown in FIG. 12, the region 3100 the attenuation coefficient of which is desired to be measured.

The echo data representative of the image 3000 are stored in the echo data memory 2400 by the received signal at the same time that the image data are stored in the image memory 1100 in response to a command from the freeze switch 1400. Let us describe the embodiment in accordance with the flowcharts of FIGS. 10(a) and (b).

The flowcharts are shown on the left side of FIGS. 10(a) and 10(b), while the results of associated processing are indicated in the form of graphs or the like on the right side at positions corresponding to relevant process steps.

The program starts with causing the arithmetic unit 2200 to read A-mode signals corresponding to region of interest 3100 out of the echo data memory 2400 at a step 4000. At a step 4002, read out A-mode signals are added and averaged along scanning direction 3200 (in FIG. 12). At a step 4004, Hamming window of predetermined width are successively applied to average value signal obtained at the step 4002 and FFT (fast Fourier transformation) are executed to obtain V(f,X). Since the width of Hamming window and the operation FFT are well kown, the description thereof are omitted.

Next, logarithm ln V(f,X) of V(f,X) are calculated at a step 4006, linear approximation are applied to change in ln V(f,X) between $X_1$ and $X_2$ of ROI at a step 4008, and then slopes $\beta(f_1)$ and $\beta(f_2)$ are found thereof by the method of least squares at a step 4010. This is, $$\beta(f_1) = \ln[V(f_1,X_1)/V(f_1,X_2)]/(X_2 - X_1)$$

$$\beta(f_2) = \ln[V(f_2,X_1)/V(f_2,X_2)]/(X_2 - X_1)$$

Accordingly, $W(f_1,F_2)X_1,X_2$ can be calculated from values $\beta(f_2)$ and $\beta(f_1)$ at a step 4012. $W(f_1,f_2)X_1,X_2$ is in the form of:

$$W(f_1,f_2)X_1,X_2 = |\beta(f_2) - \beta(f_1)|/2(f_2 - f_1) =$$

$$\frac{1}{2(X_2 - X_1)(f_2 - f_1)} \cdot \ln\left[\frac{V(f_2,X_1)}{V(f_2,X_2)} \Big/ \frac{V(f_1,X_1)}{V(f_1,X_2)}\right]$$

As previously described, above steps are also applied in measuring the data $Ws(f_1,f_2)x_1,x_2$ for standard medium similarly and the data Ws are stored in the standard data memory 2300.

We assume that we already have data $Ws(f_1,f_2)x_1,x_2$ calculated in advance in the memory 2300. Next, flow goes to a step 4014 and standard data $Ws(f_1,f_2)X_1,X_2$ are read out of standard data memory 2300.

Let us assume that we have data $Ws_i(f_1,f_2)_k$ with respect to three different standard media 1, 2, 3 in the standard data memory 2300 and each of these data are measured along minute interval $\Delta X$ between k and k+1, as shown in FIG. 11. When ROI interval $X_1-X_2$ is 3 $\Delta X$, for example, we have the following values:

$$\begin{bmatrix} Ws_1(f_1,f_2)2, & Ws_1(f_1,f_2)3, & Ws_1(f_1,f_2)4 \\ Ws_2(f_1,f_2)2, & Ws_2(f_1,f_2)3, & Ws_2(f_1,f_2)4 \\ Ws_3(f_1,f_2)2, & Ws_3(f_1,f_2)3, & Ws_3(f_1,f_2)4 \end{bmatrix}$$

From these values, $Wsi(f_1,f_2)X_1,X_2$ are obtained at a step 4016 as follows:

$$Ws_1(f_1,f_2)X_1,X_2 = \{Ws_1(f_1,f_2)2 + Ws_1(f_1,f_2)3 + Ws_1(f_1,f_2)4\}$$

$$Ws_2(f_1,f_2)X_1,X_2 = \{Ws_2(f_1,f_2)2 + Ws_2(f_1,f_2)3 + Ws_2(f_1,f_2)4\}$$

$$Ws_3(f_1,f_2)X_1,X_2 = \{Ws_3(f_1,f_2)2 + Ws_3(f_1,f_2)3 + Ws_3(f_1,f_2)4\}$$

Program goes to a step 4018 to calculate $|W(f_1,f_2)x_1,x_2 - Ws_i(f_1,f_2)x_1,x_2|$ for every i and find i that minimizes $|W(f_1,f_2)x_1,x_2 - Ws_i(f_1,f_2)x_1,x_2|$. When such i is found, $\Delta\alpha s_i$ corresponding to i is a frequency dependence of an attenuation coefficient $\Delta^\alpha$ which are sought (step 4020). We can assume that $\alpha(f,X) = \alpha o(X) \cdot f$ and $\alpha s(f,X) = \alpha os(X) \cdot f$ for soft biological tissue and standard medium similar to soft biological tissue, respectively. From Eq. (13'), we can therefore obtain from the following equations:

$$\Delta\alpha(f_1, f_2) = \frac{(f_2 - f_1)}{(X_2 - X_1)(f_2 - f_1)} \cdot \overline{\alpha o} \cdot (X_2 - X_1) = \overline{\alpha o}$$

$$\Delta\alpha s(f_1, f_2) = \frac{(f_2 - f_1)}{(X_2 - X_1)(f_2 - f_1)} \cdot \overline{\alpha so} \cdot (X_2 - X_1) = \overline{\alpha so}$$

Accordingly, we can obtain a mean attenuation coefficient $\overline{\alpha o}$ for soft biological tissue by obtaining $\Delta\alpha(f_1,f_2)$ or $\Delta\alpha s(f_1,f_2)$.

The flowcharts deal with only three standard media in order to simplfy the description of the invention. However, predictable values of attenuation coefficients of actual soft biological tissue range from about 0.1 to about 3.0 dB/cm MHz, as indicated by the following table. Therefore, more precise measurements can be made by preparing standard media having attenuation coefficients that differ by small increments within the above range of values and storing the resulting standard data in the standard data memory 2300.

| Tissue | α/f Mean Value (dB/cm MHz) | α/f Standard Deviation (dB/cm MHz) | Frequency Range (MHz) |
| --- | --- | --- | --- |
| Aqueous or vitreous humour of eye | 0.10 | — | 6–30 |
| Blood | 0.18 | — | 1.0 |
| Fat | 0.63 | 0.073 | 0.8–7.0 |
| Medulla oblongata along fibers | 0.80 | 0.071 | 1.7–3.4 |
| Brain | 0.85 | 0.056 | 0.9–3.4 |
| Liver | 0.94 | 1.058 | 0.3–3.4 |
| Kidney | 1.0 | 0.04 | 0.3–4.5 |
| Spinal cord | 1.0 | — | 1.0 |
| Medulla oblongata across fibers | 1.2 | 0.05 | 1.7–3.4 |
| Muscle, along fibers | 1.3 | 0.07 | 0.8–4.5 |
| Heart muscle | 1.8 | 0.10 | 0.3–4.5 |
| Lens of eye | 2.0 | — | 3.3–13 |
| Muscle, across fibers | 3.3 | 0.35 | 0.8–4.5 |
| Skullbone | 20 | — | 1.6 |
| Lung | 41 | — | 1.0 |

Figure 13:
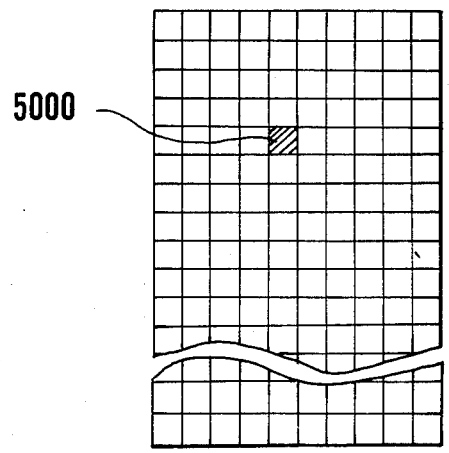
FIG. 13 is a view for describing an example of measurement of a region of interest according to another embodiment of the present invention.

Another sensible expedient is to perform the actual standard data measurement by interpolating to a certain extent to obtain standard data intermediate two actual values. Also, the standard media need not be phantoms of the kind described above but can be actual samples of biological tissue extracted from animals. Though the above description relates to a method of measuring the frequency dependence of the attenuation coefficient with regard to the region of interest 3100 of the object 400, the method can be expanded upon to provide an arrangement wherein the object 400 is divided into an imaginery matrix of the kind shown in FIG. 13 and each unit pixel 5000 of the matrix is treated as the region of interest. In other words, with such an arrangement processing in accordance with the flowcharts of FIGS. 10(a) and 10(b) is performed for one pixel after another in sequential fashion, and the calculated values are luminance modulated and displayed on the display unit 1300. The display will be a two-dimensional distribution of the attenuation coefficients of the object 400.

CONCRETE EFFECT OF THE INVENTION

According to the present invention, pulse echo signals from a plurality of standard media having different attenuation coefficients measured in advance are stored in memory, and so is the frequency dependence of the attenuation coefficients of these media measured by a different method, namely by a transmission-reflection method. The difference is found between a pulse echo signal obtained by information processing on the basis of measurements taken of a object under examination, and the stored pulse echo signals of the standard media following identical information processing. An attenuation coefficient of one of the standard media that minimizes the difference value is adopted as the attenuation coefficient of the object. It is thus possible to measure the frequency dependence of the attenuation coefficient of the object while diminishing the influence which the sound field transmitted by the transducer used in the measurements has on the attenuation coefficient.

As many apparently widely different embodiments of the present invention can be made without departing from the spirit and scope thereof, it is to be understood that the invention is not limited to the specific embodiments thereof except as defined in the appended claims.

What I claim is:

1. An ultrasonic measurement method for measuring acoustic characteristics of an object under examination by transmitting an ultrasonic pulse into the object and detecting an ultrasonic echo signal reflected from within the object, said method comprising steps of:
   preparing a plurality of standard media having attenuation coefficients that differ from one another;
   transmitting an ultrasonic pulse into each standard medium and then finding and storing in memory a first attenuation rate for each of a number of positions over a range of depths in each standard medium based on an ultrasonic echo signal from each depth;
   transmitting an ultrasonic pulse having a plurality of substantially different frequency components into each standard medium and then finding and storing in memory an attenuation coefficient based on an ultrasonic signal which has passed through each standard medium;
   transmitting an ultrasonic pulse having a plurality of different frequency components into the object;
   measuring a second attenuation rate which corresponds to a desired depth range in the object based on an ultrasonic echo signal received from within the object;
   calculating a difference between the second attenuation rate obtained for the desired depth range in the object and the first attenuation rate at the depth corresponding to the desired depth range for each of the standard media,
   finding the standard medium having an first attenuation rate that gives the minimum value of said difference; and
   finding the attenuation coefficient corresponding to said standard medium;
   wherein said attenuation coefficient corresponding to said standard medium is adopted as an attenuation coefficient over the desired depth range of the object.

2. The ultrasonic measurement method of claim 1, wherein said step of measuring the second attenuation rate comprises the steps of:

extracting two frequency-components at two frequencies from the ultrasonic echo signal received from within the desired depth range in the object;

logarithmically compressing each of the two frequency components extracted from the ultrasonic echo signal;

linearly approximating each of the logarithmically compressed frequency components;

determining slopes of straight lines, with respect to the depth direction, obtained by the linear approximation; and calculating the second attenuation rate by dividing the difference of the slopes by the difference of the two frequencies.

3. An ultrasonic measurement apparatus for measuring acoustic characteristics of an object under examination by transmitting an ultrasonic pulse into the object and detecting an ultrasonic echo signal reflected from within the object, said apparatus comprising:

ultrasonic transceiving means for transmitting an ultrasonic pulse and receiving ultrasonic signals;

memory means for storing the ultrasonic signals received by said transceiving means;

arithmetic means for operating on the received ultrasonic signals to find first and second attenuation rates and differences between attenuation rates;

and control means for controlling said transceiving means, said memory means and said arithmetic means, wherein in response to control executed by said control means, said transceiving means transmits an ultrasonic pulse into each of a plurality of standard media having attenuation coefficients that differ from one another, said arithmetic means finds the first attenuation rate for each of a number of positions over a range of depths in each standard medium based on an ultrasonic echo signal obtained from each depth and stores the attenuation rates in said memory means, said transceiving means transmits an ultrasonic pulse having a plurality of different frequency components into each standard medium, said arithmetic means finds an attenuation coefficient based on an ultrasonic signal which has passed through each standard medium and stores the attenuation coefficients in said memory means, said transceiving means transmits an ultrasonic pulse having a plurality of different frequency components into the object, said arithmetic means finds the second attenuation rate which corresponds to a desired depth range in the object based on an ultrasonic echo signal received from within the object, the first attenuation rate over a corresponding range of depths in each of the standard media is read out of said memory means, said arithmetic means calculates a difference between said first attenuation rate read out of said memory means and said second attenuation rate obtained for the desired depth range in the object, finds the standard medium having the first attenuation rate that gives the minimum value of said difference, and finds the attenuation coefficient corresponding to said standard medium, wherein said attenuation coefficient is adopted as an attenuation coefficient over the desired range of depths of the object.

4. The ultrasonic measurement apparatus of claim 3, wherein said arithmetic means includes means for finding said second attenuation rate by:

extracting two frequency-components at two frequencies from the ultrasonic echo signal received from within the desired depth range in the object;

logarithmically compressing each of the two frequency components extracted from the ultrasonic echo signal;

linearly approximating each of the logarithmically compressed frequency components;

determining slopes of straight lines, with respect to the depth direction, obtained by the linear approximation; and calculating the second attenuation rate by dividing the difference of the slopes by the difference of the two frequencies.

5. The ultrasonic measurement apparatus of claim 3, wherein the apparatus further comprises:

modulation means for brightness-modulating said attenuation coefficient which has been adopted as the attenuation coefficient over the desired range of depths; and display means for displaying the brightness-modulated attenuation coefficient.

6. An ultrasonic measurement apparatus for measuring acoustic characteristics of an object under examination by transmitting an ultrasonic pulse into the object and detecting an ultrasonic echo signal reflected from within the object, said apparatus comprising:

memory means for storing an attenuation coefficient, obtained in advance, of each of a plurality of standard media having attenuation coefficients that differ from one another, and a first attenuation rate, obtained in advance, for each of a variety of depths in each of the standard media;

ultrasonic transceiving means for transmitting an ultrasonic pulse into and receiving ultrasonic echo signals from within the object;

arithmetic means for carrying out arithmetic calculations;

and control means for controlling said transceiving means, said memory means and said arithmetic means, wherein in response to control executed by said control means, said transceiving means transmits an ultrasonic pulse having a plurality of different frequency components into the object, said arithmetic means calculates a second attenuation rate over a desired depth range in the object based on ultrasonic echo signals received from within the object, the first attenuation rate over a range of depths in each of the standard media corresponding to the range of depths in the object is read out of said memory means, said arithmetic means calculates a difference between each of the first attenuation rates read out of said memory means and the attenuation rate obtained with regard to the desired range of depths in the object and finds the standard medium having the first attenuation rate that gives the minimum value of said difference, wherein said attenuation coefficient corresponding to the standard medium found by said arithmetic means is adopted as an attenuation coefficient over the desired range of depths of the object.

7. The ultrasonic measurement apparatus of claim 6, wherein said arithmetic means includes means for finding said second attenuation rate by:
- extracting two frequency-components at two frequencies from the ultrasonic echo signal received from within the desired depth range in the object;
- logarithmically compressing each of the two frequency components extracted from the ultrasonic echo signal;
- linearly approximating each of the logarithmically compressed frequency components;
- determining slopes of straight lines, with respect to the depth direction, obtained by the linear approximation; and
- calculating the second attenuation rate by dividing the difference of the slopes by the difference of the two frequencies.

8. The ultrasonic measurement apparatus of claim 6, wherein the apparatus further comprises:
- modulation means for brightness-modulating said attenuation coefficient which has been adopted as the attenuation coefficient over the desired range of depths; and
- display means for displaying the brightness-modulated attenuation coefficient.

* * * * *

UNITED STATES PATENT AND TRADEMARK OFFICE
CERTIFICATE OF CORRECTION

PATENT NO. : 4,644,510
DATED : February 17, 1987
INVENTOR(S) : T. FUJII

It is certified that error appears in the above-identified patent and that said Letters Patent is hereby corrected as shown below:

COLUMN 6, line 47, change "nealy" to --nearly--;

COLUMN 7, line 47, "it" should read --if--;

COLUMN 8, line 3, "be" should read --been--;

COLUMN 13, line 6, "$f_1$, $F_2$" should read --$f_1$, $f_2$--;

COLUMN 16, line 11, "kown" should read --known--.

Signed and Sealed this

Twentieth Day of October, 1987

Attest:

DONALD J. QUIGG

*Attesting Officer*  *Commissioner of Patents and Trademarks*